US009018598B2

(12) United States Patent
Brechtel (10) Patent No.: US 9,018,598 B2
(45) Date of Patent: Apr. 28, 2015

(54) AEROSOL IONIZER

(71) Applicant: Brechtel Manufacturing, Inc., Hayward, CA (US)

(72) Inventor: Fredrick J Brechtel, Berkeley, CA (US)

(73) Assignee: Brechtel Manufacturing, Inc., Hayward, CA (US)

( * ) Notice: Subject to any disclaimer, the term of this patent is extended or adjusted under 35 U.S.C. 154(b) by 0 days.

(21) Appl. No.: 14/279,800

(22) Filed: May 16, 2014

(65) Prior Publication Data

US 2014/0339441 A1  Nov. 20, 2014

Related U.S. Application Data

(60) Provisional application No. 61/825,019, filed on May 18, 2013.

(51) Int. Cl.
| | |
|---|---|
| *H01J 49/10* | (2006.01) |
| *G01N 27/68* | (2006.01) |
| *G01R 29/24* | (2006.01) |
| *H01J 27/02* | (2006.01) |
| *G01N 27/62* | (2006.01) |
| *H01J 49/14* | (2006.01) |

(52) U.S. Cl.
CPC ............... *G01R 29/24* (2013.01); *H01J 27/02* (2013.01); *G01N 27/624* (2013.01); *H01J 49/145* (2013.01)

(58) Field of Classification Search
CPC ....... H01J 49/04; H01J 49/145; H01J 49/165; H01J 49/0404; H01J 49/045; H01J 49/0463; H01J 49/049; H01J 49/10; H01J 49/105; H01J 49/0431; H01J 49/168; G01N 27/624; G01N 27/68

USPC ............ 250/288, 423 R, 281, 283, 287, 424, 250/282, 324, 423 F, 423 P, 425, 427; 315/111.81

See application file for complete search history.

(56) References Cited

U.S. PATENT DOCUMENTS

| | | | | | |
|---|---|---|---|---|---|
| 4,549,082 | A | * | 10/1985 | McMillan | 250/423 R |
| 4,968,885 | A | * | 11/1990 | Willoughby | 250/288 |
| 5,285,064 | A | * | 2/1994 | Willoughby | 250/288 |
| 5,397,901 | A | * | 3/1995 | Lo | 250/424 |
| 5,400,665 | A | * | 3/1995 | Zhu et al. | 73/863.12 |
| 6,750,449 | B2 | * | 6/2004 | Marcus | 250/288 |
| 6,900,734 | B2 | * | 5/2005 | Duan | 340/632 |
| 7,462,824 | B2 | * | 12/2008 | Wang | 250/288 |
| 7,518,108 | B2 | * | 4/2009 | Frey et al. | 250/288 |
| 7,525,086 | B2 | * | 4/2009 | Suzuki | 250/288 |
| 7,815,798 | B2 | * | 10/2010 | Schliefer | 210/198.2 |
| 7,968,842 | B2 | * | 6/2011 | Zapata et al. | 250/288 |
| 8,853,626 | B2 | * | 10/2014 | Hiraoka et al. | 250/288 |
| 2006/0071177 | A1 | * | 4/2006 | Palsulich et al. | 250/423 R |
| 2007/0102634 | A1 | * | 5/2007 | Frey et al. | 250/288 |
| 2008/0067352 | A1 | * | 3/2008 | Wang | 250/288 |

(Continued)

*Primary Examiner* — David A Vanore
(74) *Attorney, Agent, or Firm* — Anters & Tormey LLP; Pete Tormey (57) ABSTRACT

A system and method comprising an ion production chamber having a plasma source disposed in said chamber, a harvest gas disposed to flow through the chamber from an inlet to an outlet, and a jet, said jet operable to introduce a sample into the harvest gas flow. In some embodiments the system includes using helium as the harvest gas. Certain embodiments include introducing a sample perpendicular to the harvest gas flow and using multiple sample introduction jets to increase mixing efficiency. The charge sample may be coupled to a MEMS-based electrometer.

14 Claims, 4 Drawing Sheets

(56) References Cited

U.S. PATENT DOCUMENTS

| | | | |
|---|---|---|---|
| 2009/0078865 A1* | 3/2009 | Zapata et al. | 250/288 |
| 2009/0250608 A1* | 10/2009 | Mordehai et al. | 250/288 |
| 2009/0297406 A1* | 12/2009 | Okino et al. | 422/116 |
| 2010/0096546 A1* | 4/2010 | Ewing et al. | 250/282 |
| 2012/0025071 A1* | 2/2012 | Mordehai et al. | 250/287 |
| 2014/0084153 A1* | 3/2014 | Schultz et al. | 250/282 |
| 2014/0271373 A1* | 9/2014 | Okino et al. | 422/119 |

\* cited by examiner

AEROSOL IONIZER

PRIORITY

This application claims the benefit of pending provisional patent application No. 61/825,019 entitled "Charged Particle Detector" by the same inventors, filed May 18, 2013 which is incorporated by reference as if fully set forth herein.

BACKGROUND

The phrase "Microelectromechanical systems" or MEMS generally describes the technology of very small devices. Conventionally MEMS are made up of components between 1 to 100 micrometers in size (i.e. 0.001 to 0.1 mm), and more typically range in size from 20 micrometers (20 millionths of a meter) to a millimeter (i.e. 0.02 to 1.0 mm). They usually consist of components that interact with the outside such as microsensors. At these small sizes MEMS raise different technological challenges. For example, because of the large surface area to volume ratio of MEMS, surface effects such as electrostatics and wetting dominate over volume effects such as inertia or thermal mass.

MEMS became practical once they could be fabricated using modified semiconductor device fabrication technologies, normally used to make electronics. These include molding and plating, wet etching (KOH, TMAH) and dry etching (RIE and DRIE), electro discharge machining (EDM), and other technologies capable of manufacturing small devices.

SUMMARY

Disclosed herein is a system and method comprising an ion production chamber having a plasma source disposed in said chamber, a harvest gas disposed to flow through the chamber from an inlet to an outlet, and a jet, said jet operable to introduce a sample into the harvest gas flow. In some embodiments the system includes using helium as the harvest gas. Certain embodiments include introducing a sample perpendicular to the harvest gas flow and using multiple sample introduction jets to increase mixing efficiency. The charge sample may be coupled to a MEMS-based electrometer.

Also disclosed is a charged particle detection system for aerosol measurements. The system may include a scanning electrical mobility sizer (SEMS), a conductive porous electrode, an electrometer based on a capacitive microelectromechanical system (MEMS), and signal processing electronics. The electrometer may be coupled to a porous conductive electrode that traps the charged particles while allowing a continuous air flow. Charge is measured using a vibrating capacitance electrometer composed of an electrostatic comb drive actuator and sense parallel plate capacitors. Particle concentrations can then be correlated to the measured charge.

The MEMS electrometer relies on the concept of the vibrating reed where one of the plates on a parallel plate capacitor is allowed to oscillate at a fixed frequency. The electrometer may consist of three parts: differential actuators, differential motion sensing, and charge modulation parallel plate capacitors. A direct current (DC) charge collected in the porous electrode may be modulated at the MEMS electrometer drive frequency and, in some embodiments, at higher harmonics due to the nonlinear nature of parallel plate capacitors. Feed-through interference from drive signals to the sensed charge may be reduced by designing the charge capacitors and detection electronics to measure a signal at twice (or some other multiple) of the drive frequency, where the feed-through signal is minimized.

DESCRIPTION

Generality of Invention

This application should be read in the most general possible form. This includes, without limitation, the following:

References to specific techniques include alternative and more general techniques, especially when discussing aspects of the invention, or how the invention might be made or used.

References to "preferred" techniques generally mean that the inventor contemplates using those techniques, and thinks they are best for the intended application. This does not exclude other techniques for the invention, and does not mean that those techniques are necessarily essential or would be preferred in all circumstances.

References to contemplated causes and effects for some implementations do not preclude other causes or effects that might occur in other implementations.

References to reasons for using particular techniques do not preclude other reasons or techniques, even if completely contrary, where circumstances would indicate that the stated reasons or techniques are not as applicable.

Furthermore, the invention is in no way limited to the specifics of any particular embodiments and examples disclosed herein. Many other variations are possible which remain within the content, scope and spirit of the invention, and these variations would become clear to those skilled in the art after perusal of this application.

Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed.

Read this application with the following terms and phrases in their most general form. The general meaning of each of these terms or phrases is illustrative, not in any way limiting.

Lexicography

The term "Aerosols" generally refers to small liquid or solid particles in a gas.

The terms "effect", "with the effect of" (and similar terms and phrases) generally indicate any consequence, whether assured, probable, or merely possible, of a stated arrangement, cause, method, or technique, without any implication that an effect or a connection between cause and effect are intentional or purposive.

The term "Electrometry" generally refers to a technique for measuring small electrical currents. Electrometer instruments are conventionally used in tunneling microscopy, mass spectrometry, and surface charge analysis. Conventional electrometers may include single-electron transistors, nanomechanical resonators at cryogenic temperatures, graphene resonators, and units based on vibrating reed devices.

The term "Flexures" generally means a bendable material designed to support a structure, but allow a predetermined amount of movement.

The term "relatively" (and similar terms and phrases) generally indicates any relationship in which a comparison is possible, including without limitation "relatively less", "relatively more", and the like. In the context of the invention, where a measure or value is indicated to have a relationship "relatively", that relationship need not be precise, need not be well-defined, need not be by comparison with any particular or specific other measure or value. For example and without limitation, in cases in which a measure or value is "relatively increased" or "relatively more", that comparison need not be with respect to any known measure or value, but might be with respect to a measure or value held by that measurement or value at another place or time.

The term "substantially" (and similar terms and phrases) generally indicates any case or circumstance in which a determination, measure, value, or otherwise, is equal, equivalent, nearly equal, nearly equivalent, or approximately, what the measure or value is recited. The terms "substantially all" and "substantially none" (and similar terms and phrases) generally indicate any case or circumstance in which all but a relatively minor amount or number (for "substantially all") or none but a relatively minor amount or number (for "substantially none") have the stated property. The terms "substantial effect" (and similar terms and phrases) generally indicate any case or circumstance in which an effect might be detected or determined.

The terms "this application", "this description" (and similar terms and phrases) generally indicate any material shown or suggested by any portions of this application, individually or collectively, and include all reasonable conclusions that might be drawn by those skilled in the art when this application is reviewed, even if those conclusions would not have been apparent at the time this application is originally filed.

The term "Stokes number" generally refers to a dimensionless number corresponding to the behavior of particles suspended in a fluid flow. The Stokes number conventionally represents the ratio of the inertial force (proportional to the mass of the particle) to the viscous force (proportional to fluid viscosity).

The terms "Ultrafine particles" or "UFPs" generally refer to nanoscale particles that are less than 100 nanometers in diameter. UFPs include both manufactured and naturally occurring particles.

MEMS Electrometer

Figure 1:
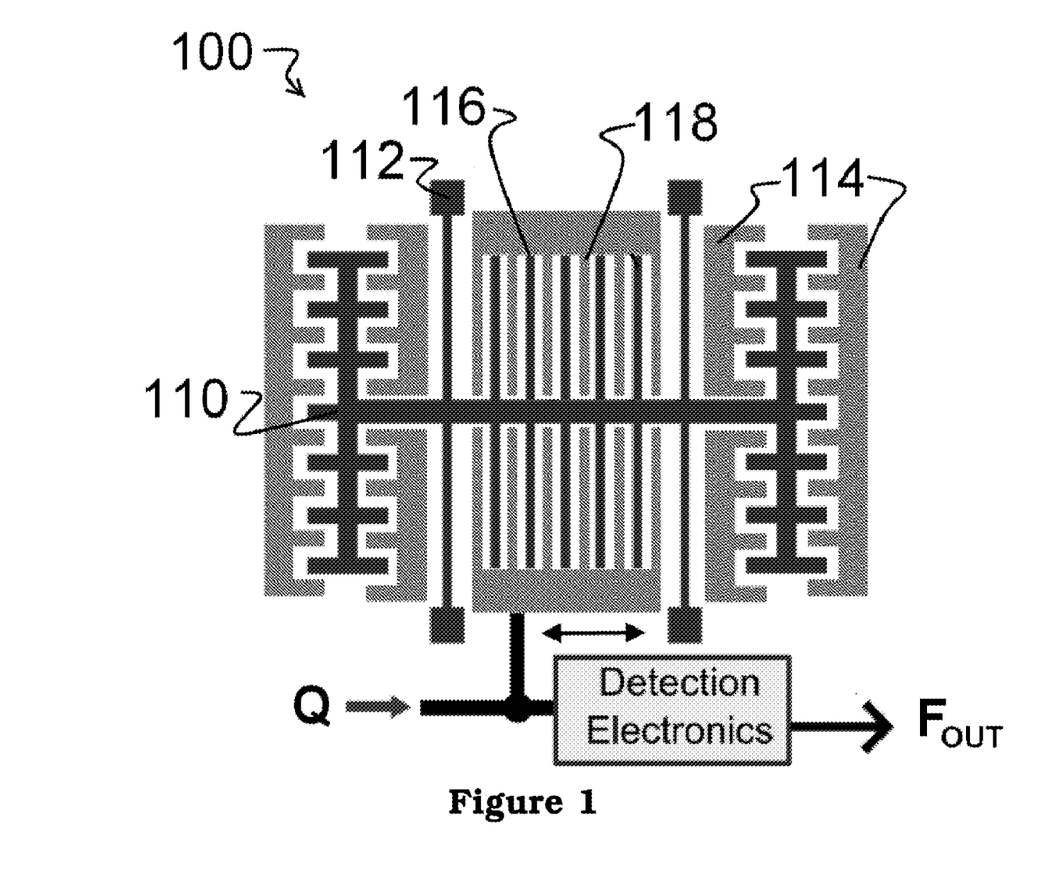
FIG. 1 illustrates a design for a MEMS device according to certain aspects of the current disclosure.

FIG. 1 illustrates a design for a MEMS device 100 according to certain aspects of the current disclosure. The device 100 includes a moving shuttle 110 supported by four flexures 112. Comb drive actuators 114 for push-pull driving of the shuttle 110 are placed at both ends of the shuttle 110. The shuttle 110 includes parallel-plate electrodes 116 disposed centrally to the shuttle 110. Interspersed between the parallel plate electrodes 116 are stationary electrodes 118 disposed independently from the shuttle 110. Together the parallel plate and stationary electrodes form a measurement capacitor (Cv).

The comb drive actuators 114 utilize electrostatic forces that act between two electrically conductive combs. Comb drive actuators conventionally operate at the micro or nanometer scale and are generally manufactured by bulk micromachining or surface micromachining a silicon wafer substrate. The attractive electrostatic forces are created when a voltage is applied between the stationary and moving combs causing them to be drawn together. The force developed by the actuator is proportional to the change in capacitance between the two combs. This force may be increased by increasing the driving voltage, the number of comb teeth, and the gap between the teeth. The teeth of the comb drive actuators 114 are arranged so that they can slide past one another until each tooth occupies the slot in the opposite comb. The flexures 112 operate as restoring springs to center the shuttle 110 when the driving voltage is removed.

The MEMS device 100 may be fabricated in 15 μm thick epitaxial polysilicon such as ST Microelectronic's ThELMA (Thick Epitaxial Layer for Micro-actuators and Accelerometers) process and vacuum sealed at the chip level. While the inventors contemplate using a shuttle 110 of 1 mm×1.2 mm, this should not be limiting because the shuttle 110 may be formed at any suitable size depending on the application.

Certain embodiments of device 110 may employ the electromechanical characteristics shown in Table 1. The measured parameters of Table 1 are derived from predetermined operating frequencies.

TABLE 1

| Parameter | Value | Units |
| --- | --- | --- |
| Spring-beam Length | 428 | μm |
| Spring-beam Width | 2.4 | μm |
| Structural Layer Thickness | 15 | μm |
| Spring Constant | 1.59 | N/m |
| Shuttle Mass | 6.58 | μg |
| Resonance $f_n$ | 2.3 | kHz |
| Comb Drive Gap | 2.6 | μm |
| No. Combs | 96 | |
| dC/dx for Comb Drive | 8.58 | nF/m |
| Sense Plate Gap | 3.6 | μm |
| Sense Plate Length | 426 | μm |
| No. Sense Plates | 66 | |
| Sense capacitance $C_V$ | 2.07468 | pF |
| Normalized Displacement $x_0$ | 0.17 | μm/μm |
| Quality Factor Q | 180 | |
| Parasitic Capacitance $C_P$ | 20 | pF |
| DC Drive voltage | 2 | V |
| AC Drive Voltage | 200 | $mV_{rms}$ |

In operation, each moving parallel-plate electrode 116 faces two stationary electrically-connected electrodes 118. When the comb drive actuators 114 are driven at a first frequency, the shuttle 110 moves causing the parallel-plate electrodes to move closer to and further from at least one of the stationary electrodes 118. The result is that the sense signal from the stationary electrodes 118 is twice the drive frequency. This provides a benefit of separating the charge drive signal from the output signal allowing for easier measurement techniques.

To maximize the capacitance variation at a given excitation voltage, driving may occur at the structure's first in-plane natural frequency, which is ideally beyond the cutoff frequency of the detection circuitry. Operating the device as a resonant sensor ensures that the electrostatic force is amplified by the mechanical quality factor Q and allows for the possibility of operating the device as a closed-loop resonator. Close-loop may be accomplished by sensing the motion of the actuator electrostatically. The sensed motion may then be employed to track the frequency of oscillation as well as the amplitude of motion. A better control on motion may provide for calibration of the electrometer to accurately increase sensitivity.

One having skill in the art will recognize that minimizing parasitic capacitance and maximizing the displacement between the stationary and moving electrodes will increase device efficiency. Moreover device mechanical architecture may include folded springs to get increased better linearity for a larger driving signal and to shift the output signal to frequencies higher than 10 kHz. This operates to provide better noise filtering characteristics.

Some embodiments of the MEMS device 100 may operate as a variable capacitor because charge placed on either of the electrode interferes with the resulting output frequency. Accordingly, detection electronics operating with the device 100 as a variable capacitor may sense charge (Qc) applied to the device 110 and provide a proportional output signal. The detection electronics may be designed to minimize systematic noise thus increasing overall performance.

References in the specification to "one embodiment", "an embodiment", "an example embodiment", etc., indicate that the embodiment described may include a particular feature, structure or characteristic, but every embodiment may not necessarily include the particular feature, structure or characteristic. Moreover, such phrases are not necessarily referring to the same embodiment. Further, when a particular feature, structure or characteristic is described in connection with an embodiment, it is submitted that it is within the knowledge of one of ordinary skill in the art to effect such feature, structure or characteristic in connection with other embodiments whether or not explicitly described. Parts of the description are presented using terminology commonly employed by those of ordinary skill in the art to convey the substance of their work to others of ordinary skill in the art.

Figure 2:
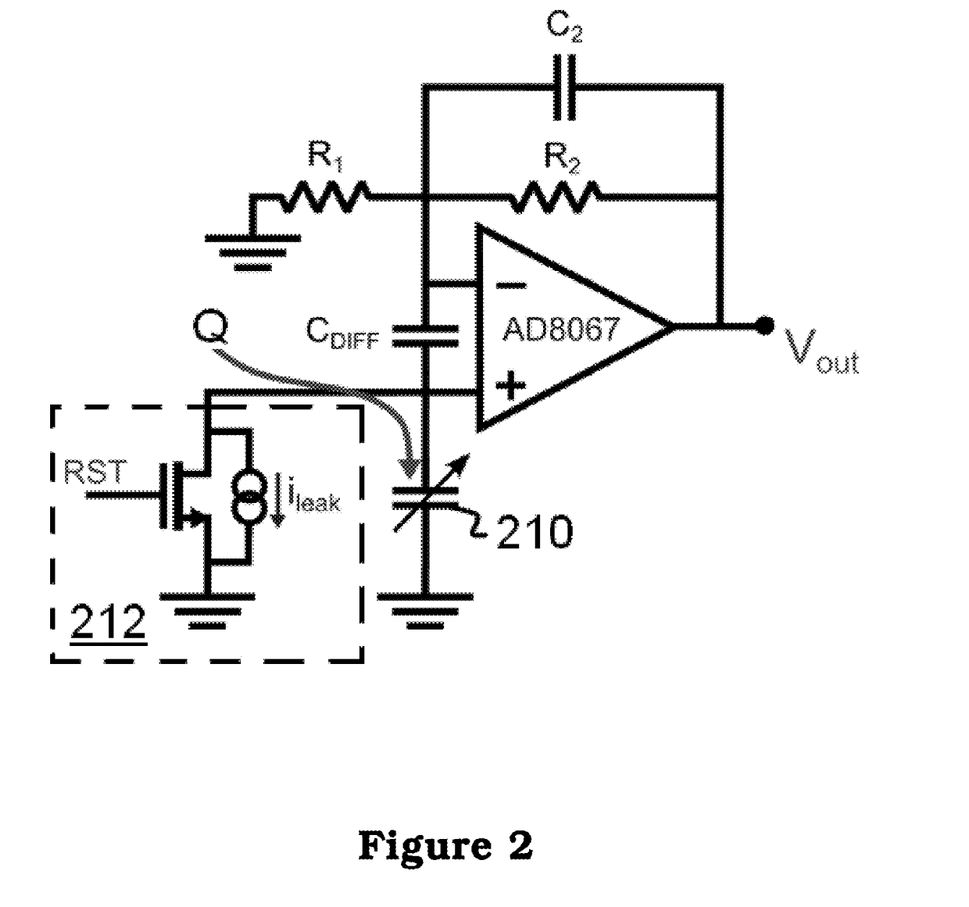
FIG. 2 shows a representative schematic of control circuitry for use in some embodiments.

FIG. 2 shows a representative schematic of control circuitry for use in some embodiments. In FIG. 2 the MEMS electrometer 210 operates as a variable capacitor altering the response of the amplifier AD8067 when charge is applied to the MEMS electrometer. Certain embodiments may contain reset circuitry 212 to discharge any accumulated charge on the variable capacitor. The reset circuitry may be effectuated using manual switches or controlled by external electronic signals. One having skill in the art will recognize that there are many different designs for measuring capacitance and charge affects on variable capacitors.

Cyclone

Figure 3:
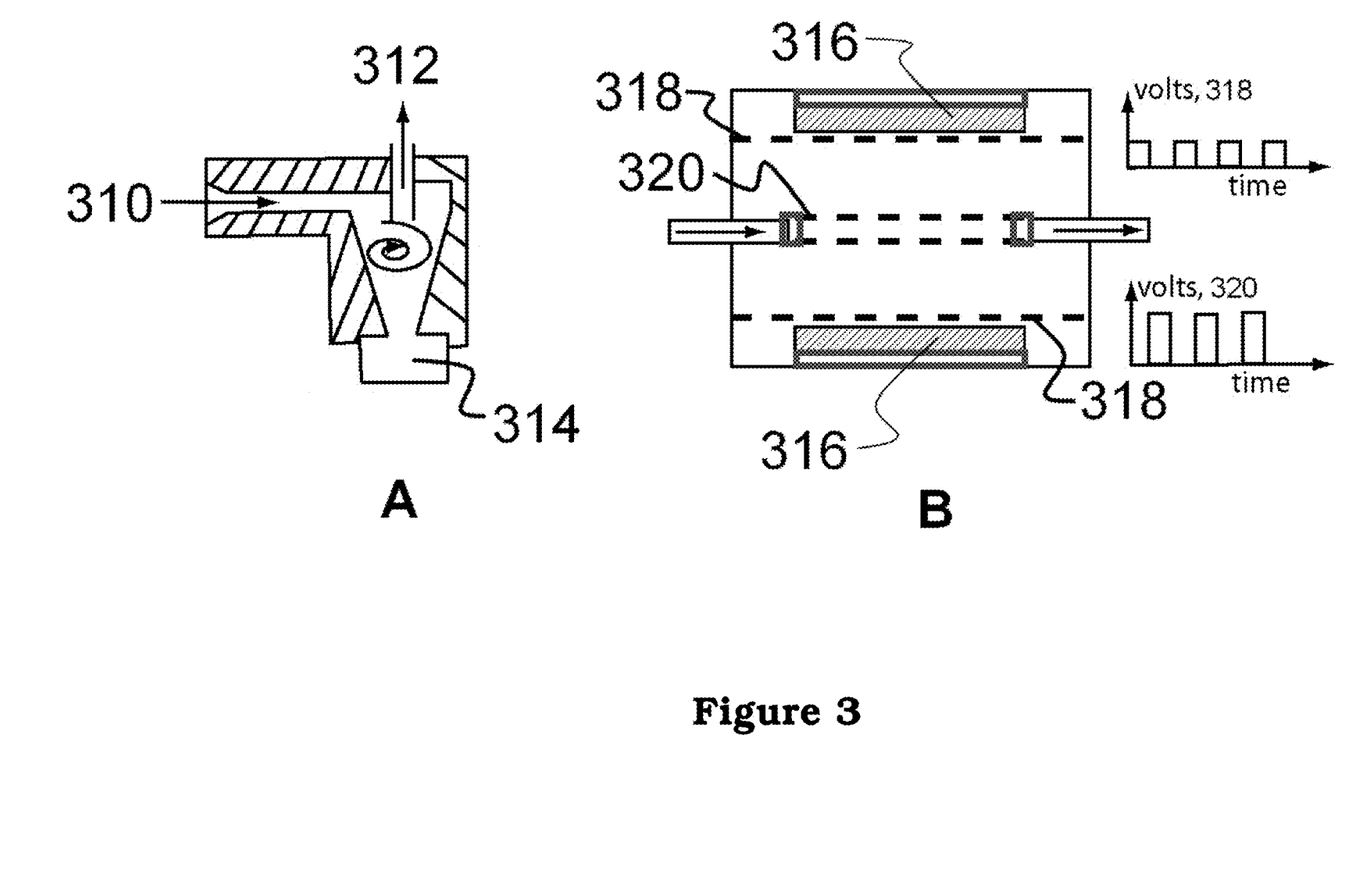
FIG. 3 shows certain elements that may form some embodiments of a charged particle detector.

FIG. 3 shows certain elements that may form some embodiments of a charged particle detector. Certain embodiments may have a device for separating sampled aerosol particles based on characteristics such as aerodynamics, electrical mobility, or other characteristic size. FIG. 3A depicts a cyclone. The cyclone accelerates particles within the Inlet Flow 310 through an inlet jet to create a spiraling airflow within the conical body. Particles with a certain minimum Stokes number have sufficient inertia to cross the streamlines and deposit on the wall or collection cup 314 at the bottom of the body. In operation, smaller particles exit through the top of the cyclone as an exit flow 312. The cyclone has the effect of removing particles larger than a so-called 'cut size' from the flow. The particle cut size may be defined as the particle size (D50) where 50% of the particles pass into the outlet flow 312 and the remaining 50% are deposited within the collection cup 314. The cut size is conventionally defined by the geometry of the cyclone and the particle Stokes number.

When particle inertial forces dominate the viscous forces exerted on the particle by the airflow, particles do not follow the air streamlines and deposit to the inside of the cyclone. Cyclones are less susceptible to clogging as compared to conventional round jet impactors, however, in some embodiments a round jet impactor may be employed to remove large particles. Alternative embodiments may be effectuated without a pre-impactor.

Charger

FIG. 3B illustrates the cross-section of a charger used to expose incoming particles to charged gas molecules in a reproducible manner so the particles become electrically charged. The inventors contemplate using negatively charged ions because the charging efficiency for this polarity is slightly higher than that for positive ions.

Some embodiments may employ a carefully controlled corona source 316 to generate ions. Alternative embodiments may employ positively charged particles. Some embodiments may employ radioactive materials, for example and without limitation, Polonium-210, Krypton-85 or Americium-241, as ion sources 316. Corona ion sources may be carefully isolated from the particles due to high electrostatic particle losses and irreproducible charging characteristics in the corona region.

In some embodiments microplasma may be employed as the ion source to charge nanoparticles. Microplasmas are plasmas of small dimensions which can be generated at a variety of temperatures and pressures. Conventionally, microplasmas may exist as either thermal or non-thermal plasmas. Non-thermal microplasmas that can maintain their state at standard temperatures and pressures can be relatively easily sustained and manipulated under standard conditions. Microplasmas may be effectuated using electrodes to create cathode discharges. The placement of the electrodes as well as the pressure determine the glow discharge of the microplasma. In additional, certain embodiments may include dielectrics to create dielectric barrier discharge microplasmas. The microplasmas may be excited by RF, AC or DC power sources. Certain embodiments may also include laser sources for generating microplasmas.

Microplasma may employ a very low electric field strength outside the 0.125 mm$^3$ plasma volume (0.5 mm cube), thus providing significantly higher ion source flux from the plasma compared to other methods and the relatively low energy of the ions produced may lead to greater reproducibility in charging. Moreover the fluid flow interactions between the particle-laden flow and the plasma may be much better controlled compared to corona techniques. Using a microplasma may include a small flow (0.3 lpm) of Helium or other appropriate harvest gas passing through the plasma to harvest ions and to keep air from extinguishing the plasma. The particle sample flow may be introduced through two small jets perpendicular to the ion-laden flow so mixing promotes interaction between the flows in a well defined volume. A small DC electric field may be applied to the combined exit flow to remove any remaining unattached ions that could alter the particle charge state downstream of the primary charging volume.

In FIG. 3B wire mesh electrodes 318 and 320 are stimulated with alternating DC electric fields to 'trap' particles within the center wire mesh electrode 320 so they are not lost to any surface inside the charger. For example and without limitation, a square wave such as voltages on 318 and 320 (shown) may be applied (out of phase) with voltage amplitudes between 0 and 400 volts (for 318) and 0 and 1000 volts (for 320) having the effect of driving negative ions into the particle flow region. In operation a charged particle traveling from the inlet to the outlet will be attracted to one or the other of the charges surfaces or ground. Before the desired charged particle reaches a surface (or ground), the polarity of the charge on wire mesh 318 is reversed, driving the charged particle away from the surface where it would have collided. By varying the applied voltage a predetermined mass of charged particle may be guided from the inlet to the outlet without colliding with any surface. Other, undesired, particles may be driven (or allowed) to collapse into the side walls.

Certain embodiments may also employ filtered sheath air to physically contain the particles within the center wire mesh region.

One having skill in the art will recognize that the design of the charger described herein minimizes the presence of multiply charged particles so that the primary responsibility of the impactor is to prevent build up of particulate matter inside the device. This may relax the cut size requirement so that a cut size of 300 nm, instead of 100 nm, will suffice for certain operations. For example and without limitation a 3.5 lpm air sample flow rate through the impactor, a 0.76 mm inside diameter jet will provide a cut size of approximately 300 nm with a pressure drop of about 0.2 atm.

Figure 4:
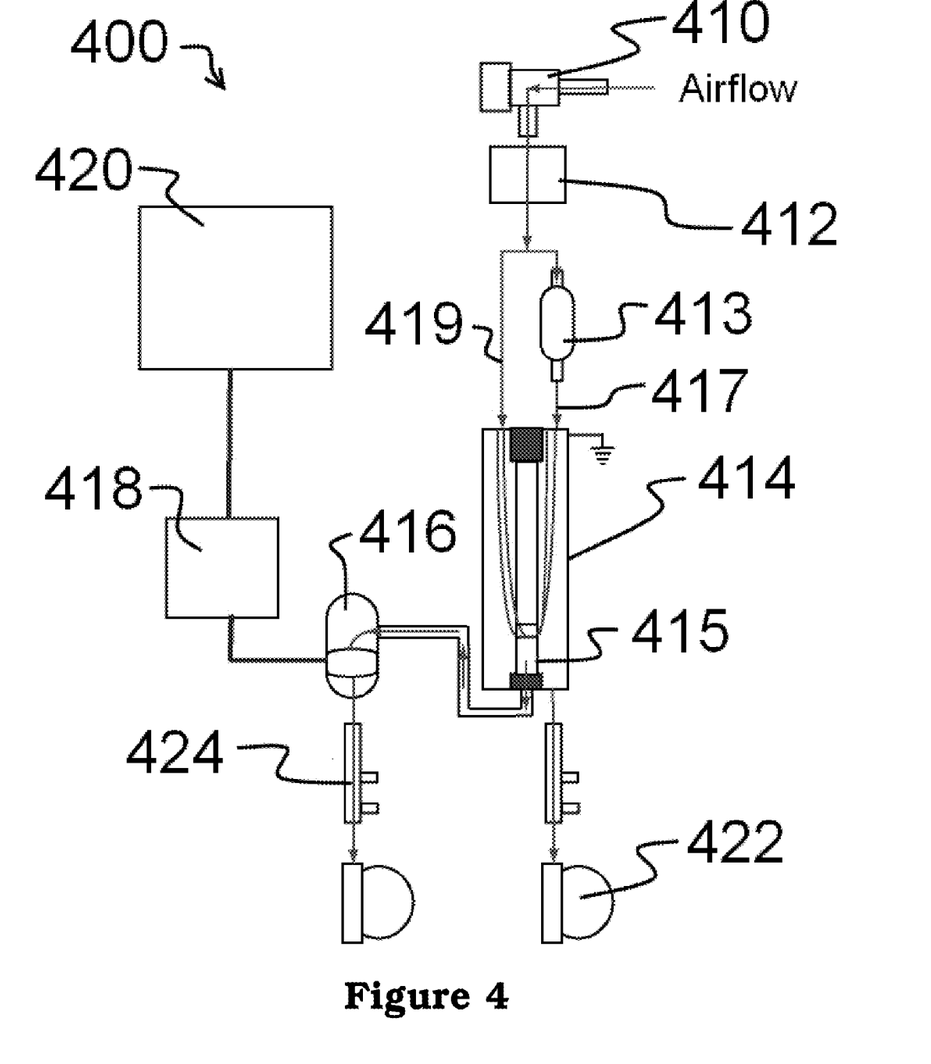
FIG. 4 illustrates one embodiment of a system for a charged particle detector.

FIG. 4 illustrates one embodiment of a system for particle number size distribution measurement 400. In FIG. 4 a cyclone 410 operates to receive an airflow. The cyclone 410 only passes particles smaller than a predetermined "cut size" for the cyclone selected. Once through the cyclone 410, the preselected particles are fed to a unipolar charger 412 for charging the particles. Now charged, the particles are applied to a sizing spectrometer 414. Before applying the airflow to a spectrometer 414, the airflow stream is split into two streams, a sheath flow 417 and a sample flow 419. In some embodiments, the split ratio is controlled to optimize the resolution of a downstream spectrometer. Once split, the sheath flow is filtered (413) to remove any particles.

Spectrometer

In some embodiments a differential mobility analyzer (DMA) type spectrometer 414 design may be employed to effectuate particle size selection. Particle size selection may be effectuated with applied high voltages that vary exponentially with time, or with high voltages varied with time in other manners, or with high voltages that are held constant with time.

In the embodiment shown, the DMA 414 may use a concentric cylinder geometry wherein the particle sample flow and filtered sheath flow pass through the annular volume between the two cylinders. In certain embodiments different DMA 414 geometry, including radial, parallel plate some heretofore unknown geometry, may be used to effectuate particle size selection. The inventors contemplate introducing the sheath and sample flows in laminar fashion to stop any fluidic mixing between the two streams. For example and without limitation, the sample flow 419 may be introduced along the inside diameter surface of an outer tube while the sheath flow 417 is introduced along the outside diameter of the inner tube. Separation may then be effectuated by applying an electric field between the inner and outer tubes and using the balance between the electric field force and viscous drag force applied to the particles to select for desired particles.

In the embodiment shown, the inside cylinder is electrically isolated from the outer cylinder and a high voltage is scanned over time using a variable high voltage supply 415 to draw charged particles toward the center cylinder surface. Small slits in the center cylinder may allow for a portion of the sheath flow to be withdrawn containing the size-selected particles.

For the spectrometer 414 size selection may be a function of geometry. For example and without limitation, the inventors have found that a center cylinder having an outside diameter of approximately 9.5 mm and a outer cylinder inside diameter of approximately 12.7 mm, about 1,074 volts are required to size select 100 nm diameter particles for a cylinder length of 51 mm. The cylinder length is the distance from the point where particles enter the spectrometer to the exit slits in the center cylinder. The above example may be effectuated under STP conditions for a filtered sheath airflow 417 of about 2 lpm and a sample flow 419 of approximately 0.36 lpm. One having skill in the art will recognize that selection of different size particles may be effectuated by varying the geometry and voltage.

In the embodiment of FIG. 4, flow is maintained by conventional miniature air flow pumps 422 and flow measurements are effectuated using conventional flow measurement equipment 424.

Some embodiments may select for size using a parallel plate design with the two electrode plates separated by insulating walls. In this embodiment one electrode plate is held at ground potential while the voltage of the other is scanned over time to draw oppositely charged particles toward it so they exit through small slits. Once the charged particles are selected, they pass to a porous charge collector 416. In another embodiment the voltage may be fixed and multiple charge collectors positioned within the device to detect different sized particles simultaneously.

Charge Collector

The charge collector 416 may be effectuated as a porous, electrically isolated metal frit electrically coupled to a MEMS electrometer 418 through a metal wire. One having skill in the art will appreciate that systemic noise may reduce performance. Accordingly shielding of the charge collector and electrometer may be critical for optimal performance. The charge collector 416 may be formed of sintered metal powder. Metal sintering may be effectuated using pure metals in a vacuum environment to reduce surface contamination. In some embodiments sintering under atmospheric pressure may be employed using a protective gas. The charge is sensed on the charge collector 416 and coupled to a MEMS electrometer 418 as described herein.

In some embodiments a collector may be formed from a 10 mm diameter, 2 mm thick disk of porous stainless steel pressed into a tube of Delrin insulator. A 1 mm diameter stainless steel wire may be inserted into the porous disk through the insulator to allow a shielded cable to be attached and supply the current signal to the electrometer 418.

Certain embodiments may employ differing control electronics 420 including but not limited to processor-based controllers and sensors for controlling the applied voltages, directing the associated airflows, and measuring the sample and excess output flows. Moreover, operation of the MEMS electrometer 418 may include low noise drive and sense circuitry which may be coupled to the processor-based controller. In addition a MEMS electrometer is shown, but certain embodiments may be effectuated using different electrometers. For example and without limitation to provide for harsher collection environments or to provide more portability of a device.

The above illustration provides many different embodiments or embodiments for implementing different features of the invention. Specific embodiments of components and processes are described to help clarify the invention. These are, of course, merely embodiments and are not intended to limit the invention from that described in the claims. Moreover the attached appendix, which is incorporated herein by reference, includes alternative embodiments.

Although the invention is illustrated and described herein as embodied in one or more specific examples, it is nevertheless not intended to be limited to the details shown, since various modifications and structural changes may be made therein without departing from the spirit of the invention and within the scope and range of equivalents of the claims. Accordingly, it is appropriate that the appended claims be construed broadly and in a manner consistent with the scope of the invention, as set forth in the following claims.

I claim:

1. A system comprising:
   an ion production chamber;
   a plasma source disposed in said chamber;
   a harvest gas disposed to flow through the chamber from an inlet to an outlet,
   a direct current electric field disposed about the outlet, and
   a jet, said jet operable to introduce a sample into the harvest gas flow.

2. The system of claim 1 wherein the harvest gas is helium.

3. The system of claim 1 wherein the sample is introduced perpendicular to the harvest gas flow.

4. The system of claim 1 wherein the plasma source includes parallel electrodes.

5. The system of claim 1 wherein the plasma source includes a dielectric.

6. The system of claim 1 further including:
   a metal electrode, said electrode coupled to an electrometer.

7. A method comprising:
   creating a microplasma;
   injecting a sample into a harvest gas;
   flowing a harvest gas through the plasma,
   wherein particles in the sample are ionized.

8. The method of claim 7 wherein the microplasma volume is less than 0.125 cubic millimeters.

9. The method of claim 7 wherein the harvest gas is helium.

10. The method of claim 7 further including:
    applying an electric field to a portion of the ionized particles.

11. The method of claim 7 wherein the harvest gas flows at substantially 0.3 lpm.

12. The method of claim 7 further including:
    applying the ionized particles to a metal charge collector, and
    coupling the charge collector to an electrometer.

13. A device comprising:
    a charger for ionizing aerosols, said charger including a microplasma;
    a porous metal charge collector coupled to the charger, and an electrometer coupled to the charge collector, said electrometer including a comb drive actuator.

14. The system of claim 13 wherein the electrometer includes a moving shuttle supported on flexures.

* * * * *